United States Patent
Lee et al.

(10) Patent No.: US 9,861,907 B2
(45) Date of Patent: *Jan. 9, 2018

(54) DIVIDED WALL DISTILLATION COLUMN FOR PRODUCING HIGH PURITY NORMAL BUTANOL, AND NORMAL BUTANOL DISTILLATION METHOD

(71) Applicant: LG CHEM, LTD., Seoul (KR)

(72) Inventors: Sung-Kyu Lee, Daejeon (KR); Joon-Ho Shin, Daejeon (KR); Jong-Ku Lee, Daejeon (KR)

(73) Assignee: LG CHEM, LTD., Seoul (KR)

(*) Notice: Subject to any disclaimer, the term of this patent is extended or adjusted under 35 U.S.C. 154(b) by 459 days.

This patent is subject to a terminal disclaimer.

(21) Appl. No.: 14/469,047

(22) Filed: Aug. 26, 2014

(65) Prior Publication Data

US 2015/0041308 A1    Feb. 12, 2015

Related U.S. Application Data

(63) Continuation of application No. 13/145,325, filed as application No. PCT/KR2010/000313 on Jan. 18, 2010, now Pat. No. 8,888,964.

(30) Foreign Application Priority Data

Jan. 20, 2009    (KR) .................. 10-2009-0004605
Jan. 14, 2010    (KR) .................. 10-2010-0003392

(51) Int. Cl.
    *B01D 3/14*    (2006.01)
    *C07C 31/12*    (2006.01)
    *C07C 29/80*    (2006.01)

(52) U.S. Cl.
CPC .............. *B01D 3/141* (2013.01); *B01D 3/14* (2013.01); *C07C 29/80* (2013.01); *C07C 31/12* (2013.01)

(58) Field of Classification Search
CPC ................................. B01D 3/141; C07C 29/80
See application file for complete search history.

(56) References Cited

U.S. PATENT DOCUMENTS 4,230,533 A * 10/1980 Giroux ................ B01D 3/14
                                                        196/132
6,846,389 B2    1/2005    Kaibel et al.
(Continued)

FOREIGN PATENT DOCUMENTS

CN    1484627    3/2004
CN    1887834    1/2007
(Continued)

OTHER PUBLICATIONS

Lee et al. "The study of structure design for dividing wall distillation column", Korean chem.. Eng. Res., vol. 45, No. 1, Feb. 2007, pp. 39-45.

(Continued)

*Primary Examiner* — Jonathan Miller
(74) *Attorney, Agent, or Firm* — Dentons US LLP

(57) ABSTRACT

The present invention relates to a dividing wall distillation column for producing high-purity n-butanol, and a method for the production of high-purity n-butanol by fractional distillation. More particularly, the present invention relates to a method which provides a dividing wall distillation column with crude n-butanol as a feed to perform a fractional distillation of n-butanol, and an apparatus thereof. The dividing wall distillation column of the present invention exhibits the effects of a two distillation column from only one distillation column, thereby reducing energy and the costs of installing the apparatus as compared to conventional distillation systems.

2 Claims, 4 Drawing Sheets

(56) References Cited

U.S. PATENT DOCUMENTS

| | | |
|---|---|---|
| 6,956,141 B1 | 10/2005 | Maas-Brunner et al. |
| 6,958,111 B2 * | 10/2005 | Rust ................... B01D 3/146 |
| | | 202/158 |
| 7,001,490 B2 * | 2/2006 | Wostbrock ............. B01D 3/141 |
| | | 196/111 |
| 7,169,267 B2 | 1/2007 | Kaibel et al. |
| 7,329,330 B2 | 2/2008 | Gall et al. |
| 7,528,290 B2 | 5/2009 | Zimmermann et al. |
| 7,670,464 B2 * | 3/2010 | Klass .................. C07C 29/82 |
| | | 203/73 |
| 8,282,793 B2 | 10/2012 | Heydrich et al. |
| 8,288,596 B2 | 10/2012 | Garton et al. |
| 2004/0000473 A1 | 1/2004 | Hofen et al. |
| 2004/0040829 A1 | 3/2004 | Gall et al. |
| 2005/0211541 A1 | 9/2005 | Bassler et al. |
| 2006/0058538 A1 | 3/2006 | Haderlein et al. |
| 2006/0151310 A1 * | 7/2006 | Klass .................. C07C 29/82 |
| | | 203/73 |

FOREIGN PATENT DOCUMENTS

| | | |
|---|---|---|
| DE | 10223974 | 12/2003 |
| JP | 2004517136 A | 6/2004 |
| KR | 10-2003-0088211 | 11/2003 |
| KR | 10-2008-0099034 | 11/2008 |
| WO | 2009000634 | 12/2008 |

OTHER PUBLICATIONS

Theories and Applications of chem.. Eng., 2008, vol. 14, No. 1, pp. 1926-1951.

* cited by examiner

【Figure 1】
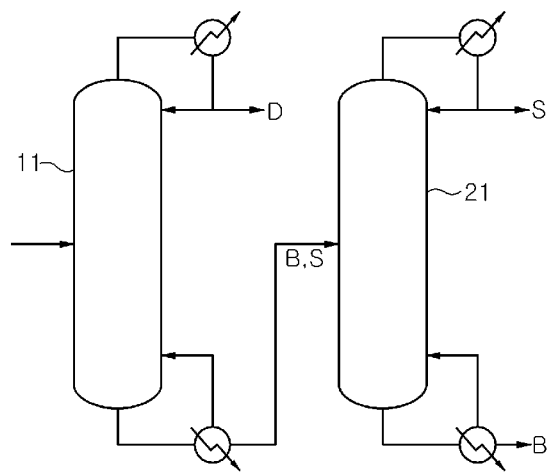
【Figure 2】
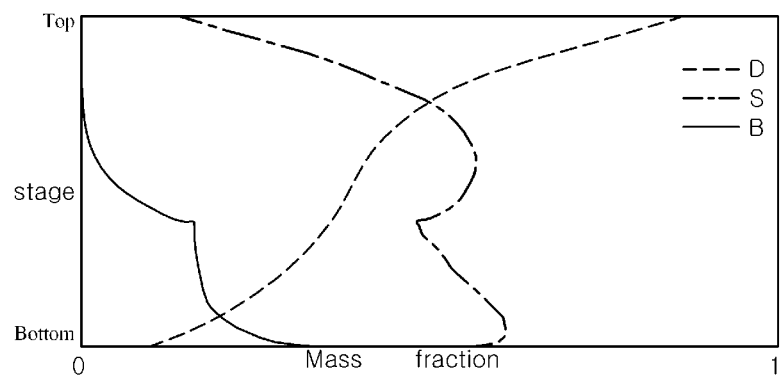
【Figure 3】
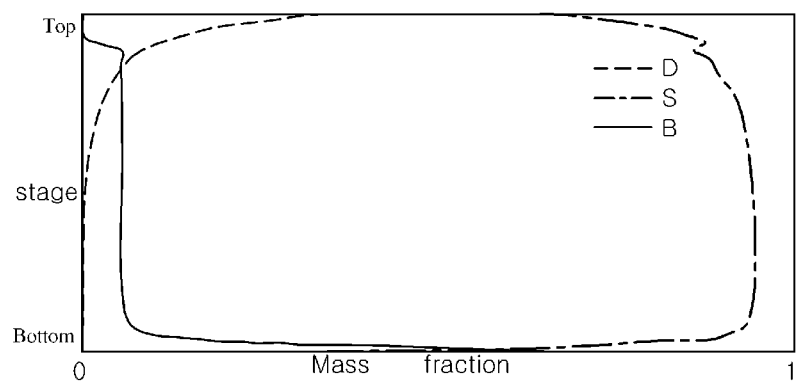

[Figure 4]
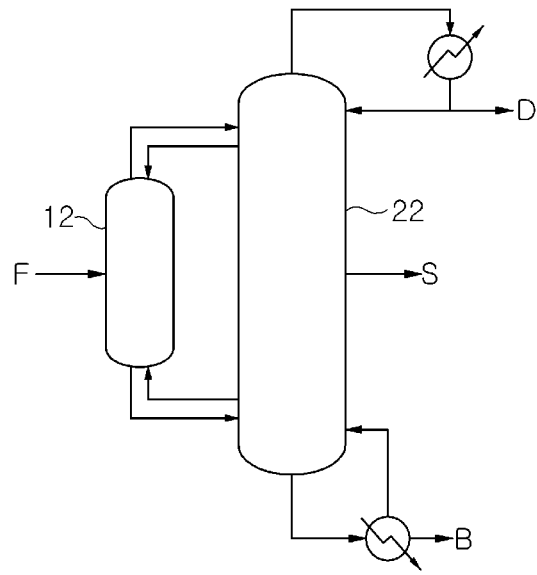
[Figure 5]
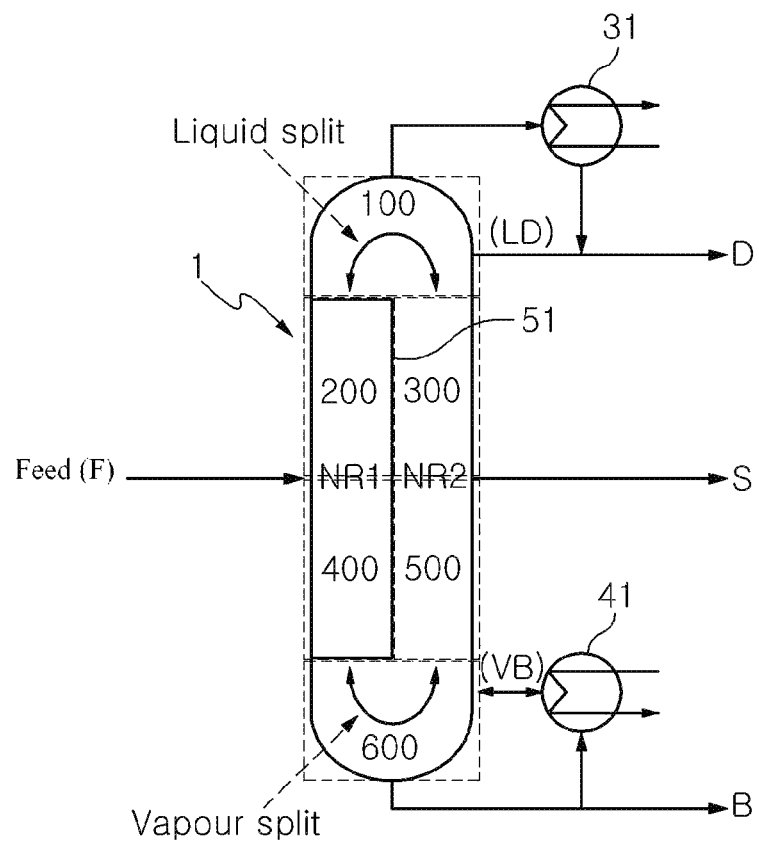

【Figure 6】
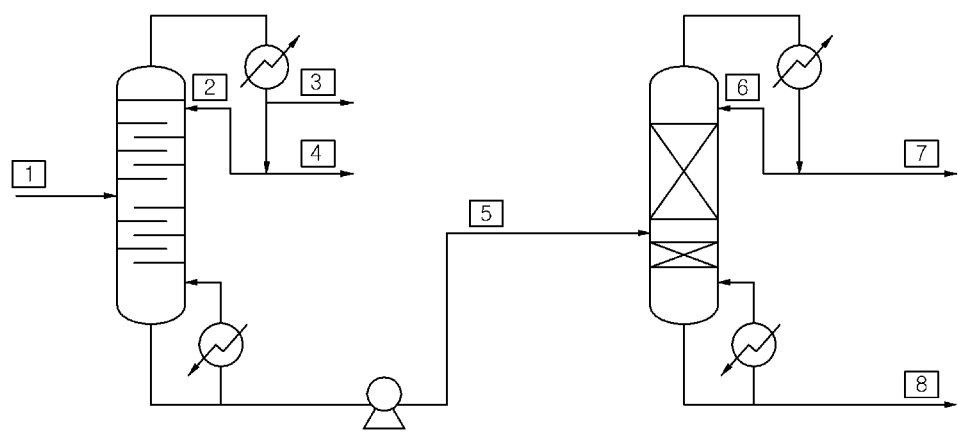

【Figure 7】
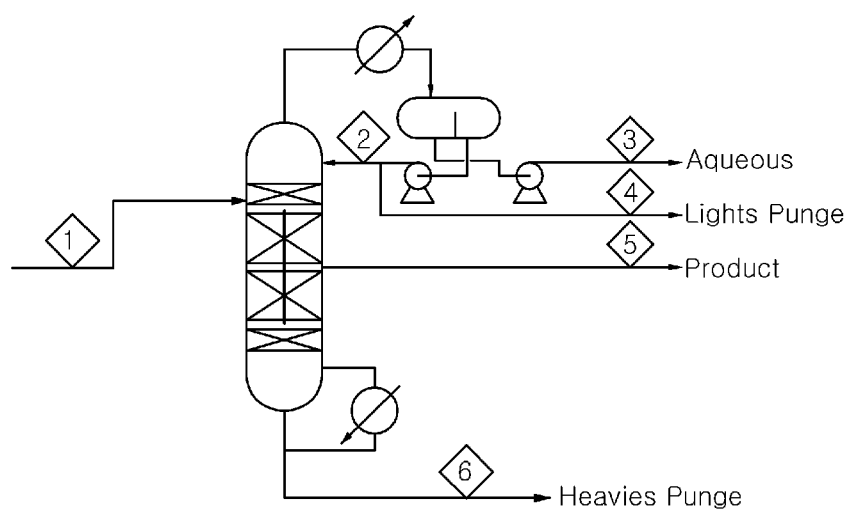

DIVIDED WALL DISTILLATION COLUMN FOR PRODUCING HIGH PURITY NORMAL BUTANOL, AND NORMAL BUTANOL DISTILLATION METHOD

This application is a continuation of application Ser. No. 13/145,325, filed Jul. 19, 2011, which is a National Stage Entry of International Application No. PCT/KR2010/000313 filed on Jan. 18, 2010 and claims the benefit of priority to Korean Patent Application No. 10-2009-0004605 filed on Jan. 20, 2009 and Korean Patent Application No. 10-2010-0003392 filed on Jan. 14, 2010, the entire disclosures of which are incorporated by reference in their entirety herein.

TECHNICAL FIELD

The present invention relates to a dividing wall distillation column for producing high-purity n-butanol, and a method for the production of high-purity n-butanol by fractional distillation.

BACKGROUND ART

Most raw materials such as crude oil are typically mixtures composed of a number of compounds. Such raw materials are rarely used without purification in industrial fields, and in most cases, they are separated into individual compounds before use. Distillation is a representative chemical process for separating mixtures into their respective components.

Generally, distillation serves to separate higher boiling components and lower boiling components from each other. (n−1) Distillation columns are required for the separation of a feed mixture composed of n components, where the number of columns is one larger than that of the components of the mixture. That is, in many cases, a conventional distillation process for the separation of a three-component mixture into its individual components employs a continuous two-column distillation system.

FIG. 1 illustrates a conventional two-column distillation system for separating a three-component mixture into the individual components.

Referring to FIG. 1, the distillation system comprises a first column 11, where a component D having the lowest boiling point is separated from a component S having the intermediate boiling point and a component B having the highest boiling point, and a second column 21, where the components S and B are separated from each other.

The composition profile in the first column is shown in FIG. 2. As shown in FIG. 2, remixing of the intermediate boiling component (S) usually occurs in the lower portion of the first column.

The conventional distillation process is advantageous in controlling the compositions of the products, but remixing of the intermediate boiling component in the first column takes place. This remixing results in low thermodynamic efficiency of the distillation column system, bringing about unnecessary additional energy consumption.

In order to solve such problems, a great deal of research has been conducted on novel distillation systems. As a representative example, a Petlyuk distillation column for improving the separation efficiency of a feed mixture, which consists of a low boiling component, an intermediate boiling component and a high boiling component, by a thermally coupled structure, is illustrated in FIG. 4. The Petlyuk distillation column comprises a preliminary separator 12 and a main separator 22, which are arranged in a thermally coupled structure. The low boiling component and the high boiling component are primarily separated from each other in the preliminary separator, and then the top and bottom products are introduced into respective feed plates of the main separator, where the low boiling component, the intermediate boiling component and the high boiling component are separated from each other. This structure increases the energy efficiency of the Petlyuk distillation column because the distillation curves in the Petlyuk distillation column become similar to the equilibrium distillation curve. However, the column is not easy to design and operate. Particularly, it is difficult to balance the internal pressures of the columns.

To overcome the limitations of Petlyuk distillation columns, dividing wall distillation columns (DWCs) have been proposed. A dividing wall distillation column is similar to a Petlyuk distillation column from a thermodynamic viewpoint, but they are structurally different from each other. A typical dividing wall distillation column has a structure in which a dividing wall is installed to integrate a preliminary separator and a main separator of a Petlyuk distillation column with each other. This structure solves the difficulties of the Petlyuk distillation column, i.e. a difficulty in balancing the pressures of the preliminary separator and the main separator of the Petlyuk distillation column and a difficulty in operating the Petlyuk distillation column. In addition, the integration of the two separators greatly lowers the investment cost of the Petlyuk distillation column.

Some distillation techniques for the production of n-butanol can be found in Korean Patent Publication No. 10-2003-0088211 A2 published on Nov. 19, 2003 ('Patent Publication 1') and Korean Patent Publication No. 10-2008-0099034 A1 published on Nov. 12, 2008 ('Patent Publication 2').

Patent Publication 1 suggests a method for purifying n-butanol using only two distillation columns. Specifically, the method comprises adding an alkaline additive to slop butanol as a raw material, which is a side product created during the production of oxoalcohol, removing water and low boiling materials from the mixture in a first distillation column 1, and removing high boiling materials from the remaining mixture in a second distillation column 2. According to the method, since the two-column distillation system produces n-butanol in an amount comparable to that of n-butanol produced by the operation of a conventional three-column distillation system, the number of processing steps is reduced and the energy and cost required to operate the two-column distillation system are greatly reduced in comparison to those of the conventional three-column distillation system.

Patent Publication 2 proposes a method comprising introducing a mixture consisting of a low boiling material A, an intermediate boiling material B and a high boiling material C into a first distillation column; separating the mixture in the first distillation column to provide a top product and a bottom product of the first distillation column to prevent remixing of the intermediate boiling material in the lower portion of the first distillation column; and separating the bottom product in the second distillation column to provide a top product and a bottom product of the second distillation column, thereby controlling the concentration ratio between the intermediate boiling material B and the low boiling material A in the top product of the second distillation column.

DISCLOSURE

Technical Problem

Dividing wall distillation columns of the prior art are not practically used in industrial fields despite their advantages. The main reason for this is that once designed, the structural disability of dividing wall distillation columns to control the internal circulating rate leads to lack of flexibility depending on variations of operational conditions, unlike Petlyuk distillation columns. That is, accurate simulation and structure determination of dividing wall distillation columns are required at the initial stage of design.

A great deal of research is currently being conducted on the structure and control of dividing wall distillation columns. However, the design structures and operational conditions of dividing wall distillation columns are very limited. Examples of the design structures of a dividing wall distillation column include the position of a feed plate, the installation zone of a dividing wall, the position of a plate where an intermediate boiling material is produced, and the total number of plates. Examples of the operational conditions of a dividing wall distillation column include distillation temperature and pressure conditions.

Particularly, the design structures (e.g., the number of plates and the position of a feed plate) and the operational conditions (e.g., distillation temperature and pressure conditions) of a dividing wall distillation column should be specially varied depending on the characteristics of a compound to be separated by fractional distillation in the dividing wall distillation column. Such limitations make it difficult to use dividing wall distillation columns.

The present invention has been made in view of the problems of the prior art. The objective of the present invention is to provide a dividing wall distillation column suitably designed to purify n-butanol with reduced energy at low installation costs. Another objective of the present invention is to provide a method for operating the dividing wall distillation column.

Technical Solution

According to an aspect of the present invention, there is provided a dividing wall distillation column comprising a condenser; a reboiler; and a main column including a dividing wall installed therein, wherein the main column is divided into a top zone, an upper feed zone, an upper outflow zone, a lower feed zone, a lower outflow zone and a bottom zone, and wherein the main column has at least one inflow and at least three outflows, the inflow being a stream of crude n-butanol as a feed F flowing into an intermediate feed plate NR1, where the upper feed zone and the lower feed zone of the main column are in contact with each other, and at least one of the outflows is substantially a stream of n-butanol.

According to another aspect of the present invention, there is provided a dividing wall distillation column comprising a condenser; a reboiler; and a main column including a dividing wall installed therein, wherein the main column is divided into a top zone, an upper feed zone, an upper outflow zone, a lower feed zone, a lower outflow zone and a bottom zone, and wherein crude n-butanol as a feed F flows into an intermediate feed plate NR1, where the upper feed zone and the lower feed zone of the main column are in contact with each other, a low boiling component D flows out of the top zone, a high boiling component B flows out of the bottom zone and an intermediate boiling component S flows out of an intermediate outflow plate NR2, where the upper outflow zone and the lower outflow zone are in contact with each other, and the intermediate boiling component S is substantially n-butanol.

In an embodiment, the feed F contains at least 90% by weight of n-butanol.

In an embodiment, the number of plates in each of the top zone, the upper feed zone, the upper outflow zone, the lower feed zone, the lower outflow zone and the bottom zone of the main column is in the range of 80 to 145% of the number of theoretical plates in the corresponding zone, as calculated by distillation curves.

In an embodiment, the length of the dividing wall is determined depending on the number of plates in the upper feed zone and the lower feed zone or the number of plates in the upper outflow zone and the lower outflow zone.

In an embodiment, the dividing wall has a length in the range of 30 to 85% of the total number of theoretical plates in the top zone, the upper feed zone, the lower outflow zone and the bottom zone, as calculated by distillation curves.

In an embodiment, the temperature of the top zone is in the range of 90 to 100° C. at ambient pressure.

In an embodiment, the temperature of the bottom zone is in the range of 140 to 160° C. at ambient pressure.

In an embodiment, the temperature of the intermediate outflow plate NR2, which is provided in a position where the upper outflow zone and the lower outflow zone are in contact with each other and from which the intermediate boiling component S flows, is in the range of 118 to 127° C. at ambient pressure.

In an embodiment, the temperature of the top zone is in the range of a lower limit temperature $T_{1a}$ to an upper limit temperature $T_{2a}$, as calculated by the following equations 1:

$$T_{1a}=86.8036 \times P^{0.3570}$$

$$T_{2a}=96.8276 \times P^{0.3201} \tag{1}$$

wherein $T_{1a}$ and $T_{2a}$ represent a temperature expressed in degrees Celsius (° C.), and P represents a pressure expressed in kgf/cm² and is from 0.1 to 10, with the proviso that P is not 1.09.

In an embodiment, the temperature of the bottom zone is in the range of a lower limit temperature $T_{1b}$ to an upper limit temperature $T_{2b}$, as calculated by the following equations 2:

$$T_{1b}=139.100 \times P^{0.1438}$$

$$T_{2b}=156.9071 \times P^{0.1977} \tag{2}$$

wherein $T_{1b}$ and $T_{2b}$ represent a temperature expressed in degrees Celsius (° C.), and P represents a pressure expressed in kgf/cm² and is from 0.1 to 10, with the proviso that P is not 1.09.

In an embodiment, the temperature of the intermediate outflow plate NR2, which is provided in a position where the upper outflow zone and the lower outflow zone are in contact with each other and from which the intermediate boiling component S flows, is in the range of a lower limit temperature $T_{1c}$ to an upper limit temperature $T_{2c}$, as calculated by the following equations 3:

$$T_{1c}=115.7594 \times P^{0.2297}$$

$$T_{2c}=125.0420 \times P^{0.2727} \tag{3}$$

wherein $T_{1c}$ and $T_{2c}$ represent a temperature expressed in degrees Celsius (° C.), and P represents a pressure expressed in kgf/cm² and is from 0.1 to 10, with the proviso that P is not 1.09.

According to yet another aspect of the present invention, there is provided a method for producing n-butanol from crude n-butanol as a feed F by fractional distillation in a dividing wall distillation column, wherein the dividing wall distillation column comprises a condenser; a reboiler; and a main column including a dividing wall installed therein, the main column being divided into a top zone, an upper feed zone, an upper outflow zone, a lower feed zone, a lower outflow zone and a bottom zone, and wherein a low boiling component D flows out of the top zone, a high boiling component B flows out of the bottom zone and an intermediate boiling component S flows out of an intermediate outflow plate NR2, where the upper outflow zone and the lower outflow zone are in contact with each other, and the intermediate boiling component S is substantially n-butanol.

In an embodiment, the feed F contains at least 90% by weight of n-butanol.

In an embodiment, the number of plates in each of the top zone, the upper feed zone, the upper outflow zone, the lower feed zone, the lower outflow zone and the bottom zone of the main column is in the range of 80 to 145% of the number of theoretical plates in the corresponding zone, as calculated by distillation curves.

In an embodiment, the length of the dividing wall is determined depending on the number of plates in the upper feed zone and the lower feed zone or the number of plates in the upper outflow zone and the lower outflow zone.

In an embodiment, the dividing wall has a length in the range of 30 to 85% of the total number of theoretical plates in the top zone, the upper feed zone, the lower outflow zone and the bottom zone, as calculated by distillation curves.

In an embodiment, the temperature of the top zone is in the range of 90 to 100° C. at ambient pressure.

In an embodiment, the temperature of the bottom zone is in the range of 140 to 160° C. at ambient pressure.

In an embodiment, the temperature of the intermediate outflow plate NR2, which is provided in a position where the upper outflow zone and the lower outflow zone are in contact with each other and from which the intermediate boiling component S flows, is in the range of 118 to 127° C. at ambient pressure.

In an embodiment, the temperature of the top zone is in the range of a lower limit temperature $T_{1a}$ to an upper limit temperature $T_{2a}$, as calculated by the following equations 1:

$$T_{1a}=86.8036 \times P^{0.3570}$$

$$T_{2a}=96.8276 \times P^{0.3201} \quad (1)$$

wherein $T_{1a}$ and $T_{2a}$ represent a temperature expressed in degrees Celsius (° C.), and P represents a pressure expressed in kgf/cm² and is from 0.1 to 10, with the proviso that P is not 1.09.

In an embodiment, the temperature of the bottom zone is in the range of a lower limit temperature $T_{1b}$ to an upper limit temperature $T_{2b}$, as calculated by the following equations 2:

$$T_{1b}=139.100 \times P^{0.1438}$$

$$T_{2b}=156.9071 \times P^{0.1977} \quad (2)$$

wherein $T_{1b}$ and $T_{2b}$ represent a temperature expressed in degrees Celsius (° C.), and P represents a pressure expressed in kgf/cm² and is from 0.1 to 10, with the proviso that P is not 1.09.

In an embodiment, the temperature of the intermediate outflow plate NR2, which is provided in a position where the upper outflow zone and the lower outflow zone are in contact with each other and from which the intermediate boiling component S flows, is in the range of a lower limit temperature $T_{1c}$ to an upper limit temperature $T_{2c}$, as calculated by the following equations 3:

$$T_{1c}=115.7594 \times P^{0.2297}$$

$$T_{2c}=125.0420 \times P^{0.2727} \quad (3)$$

wherein $T_{1c}$ and $T_{2c}$ represent a temperature expressed in degrees Celsius (° C.), and P represents a pressure expressed in kgf/cm² and is from 0.1 to 10, with the proviso that P is not 1.09.

Advantageous Effects

The dividing wall distillation column of the present invention has the same effects as two-column distillation systems from only one distillation column. Therefore, the dividing wall distillation column of the present invention possesses the advantages of reduced energy consumption and low installation costs, compared to conventional distillation systems.

DESCRIPTION OF DRAWINGS

FIG. 1 is a schematic view illustrating a conventional distillation system for separating a three-component mixture;

FIG. 2 shows the composition profile in a first column of the distillation system of FIG. 1;

FIG. 3 shows the composition profile in a conventional one-column distillation system that is operated with a lateral outflow;

FIG. 4 is a schematic view illustrating the structure of a Petlyuk distillation column;

FIG. 5 is a schematic view illustrating the structure of a dividing wall distillation column according to an embodiment of the present invention;

FIG. 6 is a schematic view illustrating a comparative distillation column system; and FIG. 7 is a schematic view illustrating an inventive dividing wall distillation column.

EXPLANATION OF ESSENTIAL PARTS OF THE DRAWINGS

| | |
|---|---|
| 1: Main column | 11: First column |
| 21: Second column | 12: Preliminary separator |
| 22: Main separator | 31: Condenser |
| 41: Reboiler | 51: Dividing wall |
| 100: Top zone | 200: Upper feed zone |
| 300: Upper outflow zone | 400: Lower feed zone |
| 500: Lower outflow zone | 600: Bottom zone |
| NR1: Intermediate feed plate | NR2: Intermediate outflow plate |
| F: Feed | B: High boiling material |
| D: Low boiling material | S: Intermediate boiling material |

BEST MODE

Hereinafter, the present invention will be explained in more detail with reference to the following examples. However, these examples are provided for illustrative purposes only and are not intended to limit the scope of the present invention.

EXAMPLES

An inventive dividing wall distillation column (DWC) using a single column was designed, constructed and operated as proposed in the present invention to verify its performance. As a result, it was confirmed that a desired composition of the final product was obtained. A comparative two-column distillation system having no dividing wall was constructed.

FIGS. 6 and 7 illustrate the comparative distillation system and the inventive dividing wall distillation column, respectively. Reference numerals 1 to 8 in FIG. 6 indicate individual streams of the comparative distillation system, and reference numerals 1 to 6 in FIG. 7 indicate individual streams in the inventive dividing wall distillation column.

The numbers of theoretical plates in the zones of the inventive dividing wall distillation column and the zones of the comparative distillation system are shown in Table 2. The experimental results are shown in Tables 3 and 4. The top zone of the inventive dividing wall distillation column had a temperature of about 95° C. The streams 2, 3 and 4 having passed through a condenser in the inventive dividing wall distillation column were cooled to about 50° C.

TABLE 2

| | Zone | Number of theoretical plates |
|---|---|---|
| Inventive dividing wall distillation column | Top zone 100 | 10 |
| | Upper feed zone 200 | 5 |
| | Upper outflow zone 300 | 10 |
| | Lower feed zone 400 | 25 |
| | Lower outflow zone 500 | 20 |
| | Bottom zone 600 | 15 |
| Comparative distillation system | First column | 20 |
| | Second column | 32 | distillation column increased, resulting in efficient production of n-butanol having a purity of 99.9 wt %. Due to the increased purity of the product, the number of additional rectification recycle steps of n-butanol was reduced and the productivity of n-butanol was improved. The inventive dividing wall distillation column, which comprises a single column and two heat exchangers, was advantageous in terms of investment cost when compared to the comparative distillation column system, which comprises two columns and four heat exchangers. In addition, the inventive dividing wall distillation column showed a 30.4% reduction rate in energy consumption compared to the comparative distillation column system.

MODE FOR INVENTION

The present invention will now be described in detail.

FIG. 5 illustrates the structure of a dividing wall distillation column according to an embodiment of the present invention. The invention will be better understood with reference to FIG. 5 and the following explanation.

The dividing wall distillation column comprises a condenser; a reboiler; and a main column including a dividing wall installed therein, wherein the main column is divided into a top zone, an upper feed zone, an upper outflow zone, a lower feed zone, a lower outflow zone and a bottom zone, and wherein the main column has at least one inflow and at least three outflows, the inflow being a stream of crude n-butanol as a feed F flowing into an intermediate feed plate NR1, where the upper feed zone and the lower feed zone of the main column are in contact with each other, and at least one of the outflows is substantially a stream of n-butanol.

TABLE 3

| | | | Unit | 1 | 2 | 3 | 4 | 5 | 6 | 7 | 8 |
|---|---|---|---|---|---|---|---|---|---|---|---|
| Comparative distillation system | Conditions | Temp. | ° C. | 87 | 97 | 97 | 97 | 129.7 | 50 | 50 | 150.2 |
| | | Pressure | Kgf/cm² | 5 | 1.09 | 1.09 | 1.09 | 4.033 | 1.79 | 1.79 | 1.874 |
| | | Flow rate | kg/hr | 15823 | 3430 | 86.5 | 65.5 | 15671 | 23268.2 | 15208 | 463 |
| | Composition | H₂O | wt % | 0.6 | 8.7 | 100 | 8.7 | 0 | 0 | 0 | 0 |
| | | Light | | 0.11 | 2.6 | 0 | 2.6 | 0.1 | 0.1 | 0.1 | 0 |
| | | n-BuOH | | 97.3 | 88.7 | 0 | 88.7 | 97.9 | 99.9 | 99.9 | 30.9 |
| | | Heavies | | 2 | 0 | 0 | 0 | 2 | 0 | 0 | 69 |
| Inventive dividing wall distillation column | Conditions | Temp. | ° C. | 87 | 50 | 50 | 50 | 122.6 | 149.7 | — | — |
| | | Pressure | kgf/cm² | 5 | 1.09 | 1.09 | 1.09 | 1.235 | 1.54 | — | — |
| | | Flow rate | kg/hr | 15823 | 13910 | 82.5 | 131.5 | 15208 | 401 | — | — |
| | Composition | H₂O | wt % | 0.6 | 41.7 | 79.4 | 18.1 | 0 | 0 | — | — |
| | | Light | | 0.11 | 3 | 0.8 | 4.25 | 0.05 | 0 | — | — |
| | | n-BuOH | | 97.3 | 55.3 | 19.8 | 77.6 | 99.9 | 20.8 | — | — |
| | | Heavies | | 2 | 0 | 0 | 0 | 0.02 | 79.12 | — | — |

TABLE 4

| | Comparative distillation system | | | Inventive dividing wall distillation column | Reduced amount (MMKcal/hr) | Reduction rate (%) |
|---|---|---|---|---|---|---|
| | Total | First column | Second column | | | |
| Amount of energy consumed (MMKcal/hr) | 7.90 | 1.21 | 6.69 | 5.50 | 2.40 | 30.4 |

As can be seen from the above results, remixing was prevented in the inventive dividing wall distillation column and the separation efficiency of the inventive dividing wall In an alternative embodiment, there is provided a dividing wall distillation column comprising a condenser; a reboiler; and a main column including a dividing wall installed therein, wherein the main column is divided into a top zone, an upper feed zone, an upper outflow zone, a lower feed zone, a lower outflow zone and a bottom zone, and wherein crude n-butanol as a feed F flows into an intermediate feed plate NR1 where the upper feed zone and the lower feed zone of the main column are in contact with each other, a low boiling component D flows out of the top zone, a high boiling component B flows out of the bottom zone and an intermediate boiling component S flows out of an intermediate outflow plate NR2, where the upper outflow zone and the lower outflow zone are in contact with each other, and the intermediate boiling component S is substantially n-butanol.

The dividing wall distillation column of the present invention comprises a condenser 31 and a reboiler 41.

The condenser 31 is a unit that absorbs heat of vaporization from a gaseous mixture to condense the gaseous mixture. The condenser 31 may be any suitable condenser used among conventional chemical engineering equipment.

The reboiler 41 is a unit that provides heat of vaporization to a liquid mixture to vaporize the liquid mixture. The reboiler 41 may be any suitable reboiler used among conventional chemical engineering equipment.

The main column 1 can be largely divided into six zones.

The top zone 100 indicates an upper region of the main column that is not partitioned by the dividing wall.

The upper feed zone 200 is a sub-region that is partitioned by the dividing wall at one side thereof and is positioned over the stream of the inflowing material (i.e. the feed).

The upper outflow zone 300 is a sub-region that is partitioned by the dividing wall at one side thereof and is positioned over the stream of the outflowing material.

The lower feed zone 400 is a sub-region that is partitioned by the dividing wall at one side thereof and is positioned under the stream of the inflowing material.

The lower outflow zone 500 is a sub-region that is partitioned by the dividing wall at one side thereof and is positioned under the stream of the outflowing material.

The bottom zone 600 indicates a lower region of the main column that is not partitioned by the dividing wall.

The main column has at least one inflow and at least three outflows.

The feed F (i.e. crude n-butanol) flows into the intermediate feed plate NR1, where the upper feed zone and the lower feed zone of the main column are in contact with each other, the low boiling component D flows out of the top zone, a high boiling component B flows out of the bottom zone, and the intermediate boiling component S flows out of the intermediate outflow plate NR2, where the upper outflow zone and the lower outflow zone are in contact with each other. The intermediate boiling component S flowing out of the intermediate outflow plate NR2 is substantially n-butanol.

The term "crude n-butanol" as used herein refers to a mixture containing n-butanol as a main component and is a material to be distilled in the dividing wall distillation column. The term "main component" means a component that composes the larger portion of the mixture than the other components of the mixture. A higher content of n-butanol in the crude n-butanol is preferred for higher purity. It is preferred to use crude n-butanol having an n-butanol content of at least 90 wt % in order to obtain n-butanol having purity as high as 99 wt %.

The phrase "substantially n-butanol" means that the mixture per se can be substantially considered as n-butanol. Specifically, the phrase means that n-butanol as a main component is present in an amount larger than the n-butanol content of the feed and exceeding at least 90 wt % with respect to the total weight of the mixture.

The structural difference between dividing wall distillation and continuous two-column distillation accounts for the reason why dividing wall distillation consumes less energy than the continuous two-column distillation. In the dividing wall distillation column, the spaces divided by the dividing wall serve as preliminary separators to separate the high boiling material and the low boiling material. This separation renders the liquid composition coinciding with the equilibrium distillation curve and inhibits the occurrence of remixing, leading to improved thermodynamic efficiency for separation.

The upper feed zone and the lower feed zone of the dividing wall distillation column act like preliminary separators of the conventional distillation column. The upper and lower feed zones of the dividing wall distillation column can be collectively referred to as a preliminary separation region. Three components flowing into the preliminary separation region are separated into a low boiling material and a high boiling material. The low boiling material and a portion of the high boiling material flow into the top zone, and portions thereof flow into the upper outflow zone and the lower outflow zone, where they are re-distilled.

The upper and lower outflow zones act like main separators of the conventional distillation column. The upper and lower outflow zones of the dividing wall distillation column can be collectively referred to as a main separation region. The low boiling material and the intermediate boiling material are predominantly separated in the upper portion of the main separation region. The intermediate boiling material and the high boiling material are predominantly separated in the lower portion of the main separation region.

After the low boiling component passes through the top zone of the main column and the condenser, a portion of the low boiling component is produced as a low boiling product D and the other portion thereof returns in the form of a liquid stream LD to the top zone of the main column. After the high boiling component passes through the bottom zone of the main column and the reboiler, a portion of the high boiling component is produced as a high boiling product B and the other portion thereof returns in the form of a vapor stream VB to the bottom zone of the main column.

The design of the thermally coupled distillation column system having the dividing wall therein is based on the design of the conventional thermally coupled distillation column having a minimum number of plates. The efficiency of the distillation column reaches a maximum value when the liquid composition distribution in the distillation plate of the column is close to the equilibrium distillation curve. Based on this, the distillation system of the present invention is designed to have a minimum number of plates on the assumption that the distillation column is operated by total reflux distillation. That is, the upper feed zone and the lower feed zone are designed under an assumption that the liquid composition is the same as the feed composition in the liquid in the feed plate, and the upper outflow zone and the lower outflow zone are designed by calculating the liquid compositions in the column from the middle portion to the top of the column, starting from the concentration of the intermediate boiling product, by a stepwise equilibration design method, and the lower outflow zone acting as a main separator is designed by stepwise calculating the liquid compositions in the column from the middle portion to the bottom of the column, starting from the concentration of the intermediate boiling product, by an equilibration design method. From the obtained liquid composition distribution, the feed plate and the numbers of plates having the compositions of the respective products can be counted to determine the numbers of plates in the upper and lower feed zones acting as preliminary separators and the number of plates in the upper and lower outflow zones acting as main separators. The number of plates in the respective zones is a theoretical and ideal value. In an actual case, it is preferred to adjust the number of plates in the column to 80 to 145% of the number of theoretical plates in accordance with common design criteria. If the number of plates in the column is less than 80% of the calculated number of theoretical plates, the low boiling material and the high boiling material may not be sufficiently separated from each other in the preliminary separation region. Meanwhile, if the number of plates in the column exceeds 145% of the calculated number of theoretical plates, which corresponds to the minimum reflux ratio, the investment costs undesirably increases without a further reduction in energy consumption.

The length of the dividing wall installed in the main column is determined depending on the number of plates calculated from the distillation curves of the upper feed zone and the lower feed zone or the upper outflow zone and the lower outflow zone.

The number of theoretical plates and the refluxed amount in the dividing wall distillation column can be calculated by various methods, for example, by plotting equilibrium distillation curves with respect to the liquid compositions in the preliminary separation region and the main separation region to design an optimum zone for the dividing wall in the dividing wall distillation column. The number of theoretical plates in the dividing wall distillation column of the present invention is determined by the Fenske-Underwood equation, which is well known to those ordinarily skilled in the art.

It is preferred that the length of the dividing wall be within the range of 30 to 85% of the total number of theoretical plates in the top zone, the upper feed zone, the lower outflow zone and the bottom zone, as calculated by distillation curves. If the length of the dividing wall is less than 30% of the number of theoretical plates, a portion of the low boiling material may fall down from the preliminary separation region and may be included in the product of the main separator. Meanwhile, if the length of the dividing wall is more than 85% of the number of theoretical plates, it is difficult to maintain smooth equilibrium flows of the liquid/vapor of the low/intermediate boiling materials and the liquid/vapor of the intermediate/high boiling materials, which may cause problems in the construction of the column.

The temperature of the top zone of the main column is preferably in the range of 90 to 100° C. at ambient pressure. If the top zone has a temperature lower than 90° C., the low boiling material may fall down from the preliminary separation region to adversely affect the purity of the product. Meanwhile, if the top zone has a temperature higher than 100° C., the high boiling material (heavies) may ascend the preliminary separation region to adversely affect the purity of the product.

The temperature of the bottom zone of the main column is preferably in the range of 140 to 160° C. at ambient pressure. If the bottom zone has a temperature lower than 140° C., the intermediate boiling material (n-butanol) falls down, resulting in a low yield of the product. Meanwhile, if the bottom zone has a temperature higher than 160° C., there is the danger that the high boiling material (i.e. heavies) may flow laterally out of the column, together with the intermediate boiling material (n-butanol).

The temperature of the intermediate outflow plate NR2, which is provided in a position where the upper outflow zone and the lower outflow zone are in contact with each other, and from which the intermediate boiling component S flows, is in the range of 118 to 127° C. at ambient pressure. If the intermediate outflow plate has a temperature lower than 118° C., it is not easy to remove the low boiling material from the intermediate outflow plate. Meanwhile, if the intermediate outflow plate has a temperature higher than 127° C., it is not easy to remove the high boiling material from the intermediate outflow plate. That is, the temperature of the intermediate outflow plate NR2 may have a great influence on the purity of the product.

The temperature ranges of the top zone, the bottom zone, and the intermediate outflow plate NR2 of the main column are values measured at ambient pressure. The ambient pressure as used herein is around 1.09 kgf/cm$^2$ and has a slightly different meaning from the atmospheric pressure (i.e. 1 atm≈1.033 kgf/cm$^2$), which is commonly understood as ambient pressure. Considering the fact that distillation columns are usually operated at pressures slightly higher than the atmospheric pressure, a pressure of about 1.09 kgf/cm$^2$ is commonly recognized as ambient pressure in chemical factories where many high-pressure processes are performed.

In the case where the dividing wall distillation column is operated at a pressure higher or lower than ambient pressure, it is necessary to control the upper limit and lower limit temperatures of the respective zones depending on the pressure. That is, the temperature ranges of the zones may be varied when the dividing wall distillation column is operated under increased or reduced pressure. Generally, the upper and lower limit temperatures tend to increase as the operating pressure increases.

For example, when the dividing wall distillation column is operated at a pressure of about 0.8 kgf/cm$^2$, it is preferred to adjust the temperature ranges of the top zone, the bottom zone and the intermediate outflow plate NR2 to about 80 to 90° C., about 135 to 150° C. and about 110 to 118° C., respectively.

When the dividing wall distillation column is operated at a pressure of about 1.3 kgf/cm$^2$, it is preferred to adjust the temperature ranges of the top zone, the bottom zone and the intermediate outflow plate NR2 to about 95 to 105° C., about 145 to 165° C. and about 123 to 135° C., respectively.

Table 1 summarizes the upper and lower limit temperatures of the top zone, the bottom zone and the intermediate outflow plate NR2 at different operating pressures of the dividing wall distillation column.

TABLE 1

|  | Lower limit Temp. (° C.) | Upper limit Temp. (° C.) |
|---|---|---|
| P ≈ 1.09 kgf/cm$^2$ (at ambient pressure) | | |
| Top zone | 90 | 100 |
| Bottom zone | 140 | 160 |
| Intermediate outflow plate NR2 | 118 | 127 |
| P ≈ 0.8 kgf/cm$^2$ (at reduced pressure) | | |
| Top zone | 80 | 90 |
| Bottom zone | 135 | 150 |
| Intermediate outflow plate NR2 | 110 | 118 |

TABLE 1-continued

|  | Lower limit Temp. (° C.) | Upper limit Temp. (° C.) |
|---|---|---|
| P ≈ 1.3 kgf/cm² (at raised pressure) | | |
| Top zone | 95 | 105 |
| Bottom zone | 145 | 165 |
| Intermediate outflow plate NR2 | 123 | 135 |

Particularly, when the top zone is not at ambient pressure, the temperature of the top zone may be in the range of a lower limit temperature $T_{1a}$ to an upper limit temperature $T_{2a}$, as calculated by the following equations 1:

$$T_{1a} = 86.8036 \times P^{0.3570}$$

$$T_{2a} = 96.8276 \times P^{0.3201} \quad (1)$$

wherein $T_{1a}$ and $T_{2a}$ represent a temperature expressed in degrees Celsius (° C.), and P represents a pressure expressed in kgf/cm² and is from 0.1 to 10, with the proviso that P is not 1.09.

When the bottom zone is not at ambient pressure, the temperature of the bottom zone may be in the range of a lower limit temperature $T_{1b}$ to an upper limit temperature $T_{2b}$, as calculated by the following equations 2:

$$T_{1b} = 139.100 \times P^{0.1438}$$

$$T_{2b} = 156.9071 \times P^{0.1977} \quad (2)$$

wherein $T_{1b}$ and $T_{2b}$ represent a temperature expressed in degrees Celsius (° C.), and P represents a pressure expressed in kgf/cm² and is from 0.1 to 10, with the proviso that P is not 1.09.

When the intermediate outflow zone NR2 is not at ambient pressure, the temperature of the intermediate outflow zone may be in the range of a lower limit temperature $T_{1c}$ to an upper limit temperature $T_{2c}$, as calculated by the following equations 3:

$$T_{1c} = 115.7594 \times P^{0.2297}$$

$$T_{2c} = 125.0420 \times P^{0.2727} \quad (3)$$

wherein $T_{1c}$ and $T_{2c}$ represent a temperature expressed in degrees Celsius (° C.), and P represents a pressure expressed in kgf/cm² and is from 0.1 to 10, with the proviso that P is not 1.09.

The above equations are derived by using the least square method based on the data in Table 1.

The thermally coupled distillation column system of the present invention aims to improve the distillation efficiency of a three-component mixture. This distillation system is constructed such that the dividing wall is installed in the main column to form spaces acting as a preliminary separator and a main separator, each of which has a liquid composition distribution similar to a high-efficiency equilibrium distillation system. Therefore, the distillation system of the present invention has the same effects as two-column distillation systems.

The present invention also provides a method for producing n-butanol from crude n-butanol as a feed by fractional distillation in a dividing wall distillation column, wherein the dividing wall distillation column comprises a condenser; a reboiler; and a main column including a dividing wall installed therein, the main column being divided into a top zone, an upper feed zone, an upper outflow zone, a lower feed zone, a lower outflow zone and a bottom zone, and wherein a low boiling component D flows out of the top zone, a high boiling component B flows out of the bottom zone and an intermediate boiling component S flows out of an intermediate outflow plate NR2, where the upper outflow zone and the lower outflow zone are in contact with each other, and the intermediate boiling component S is substantially n-butanol.

In an embodiment, the number of plates in each of the top zone, the upper feed zone, the upper outflow zone, the lower feed zone, the lower outflow zone and the bottom zone is in the range of 80 to 150% of the number of theoretical plates in the corresponding zone, as calculated by distillation curves.

In an embodiment, the length of the dividing wall is determined depending on the number of plates in the upper feed zone and the lower feed zone or the number of plates in the upper outflow zone and the lower outflow zone.

In an embodiment, the dividing wall has a length in the range of 30 to 85% of the total number of theoretical plates in the top zone, the upper feed zone, the lower outflow zone and the bottom zone, as calculated by distillation curves.

In an embodiment, the temperature of the top zone is in the range of 90 to 100° C. at ambient pressure.

In an embodiment, the temperature of the bottom zone is in the range of 140 to 160° C. at ambient pressure.

In an embodiment, the temperature of the intermediate outflow plate NR2, which is provided in a position where the upper outflow zone and the lower outflow zone are in contact with each other and from which the intermediate boiling component S flows, is in the range of 118 to 127° C. at ambient pressure.

In an embodiment, when the top zone is not at ambient pressure, the temperature of the top zone is in the range of a lower limit temperature $T_{1a}$ to an upper limit temperature $T_{2a}$, as calculated by Equations 1.

In an embodiment, when the bottom zone is not at ambient pressure, the temperature of the bottom zone is in the range of a lower limit temperature $T_{1b}$ to an upper limit temperature $T_{2b}$, as calculated by Equations 2.

In an embodiment, when the intermediate outflow plate NR2, which is provided in a position where the upper outflow zone and the lower outflow zone are in contact with each other and from which the intermediate boiling component S flows, is not at ambient pressure, the temperature of the intermediate outflow plate is in the range of a lower limit temperature $T_{1c}$ to an upper limit temperature $T_{2c}$, as calculated by Equations 3.

The invention claimed is:

1. A dividing wall distillation column comprising a condenser; a reboiler; and a main column including a dividing wall installed therein,
   wherein the main column is divided into a top zone, an upper feed zone, an upper outflow zone, a lower feed zone, a lower outflow zone and a bottom zone, and wherein the main column has at least one inflow and at least three outflows, the inflow being a stream of crude n-butanol as a feed flowing into an intermediate feed plate, where the upper feed zone and the lower feed zone of the main column are in contact with each other, and at least one of the outflows is substantially a stream of n-butanol,
   wherein a temperature of the top zone is in the range of 90 to 100° C. at ambient pressure, a temperature of an intermediate outflow plate at a position where the upper outflow zone and the lower outflow zone are in contact with each other is in the range of 118 to 127° C. at ambient pressure, and a temperature of the bottom zone is in the range of 140 to 160° C. at ambient pressure, and wherein the inflow is a stream of a feed containing at least 90% by weight of n-butanol flowing into an intermediate feed plate.

2. A method for producing a feed of n-butanol from crude n-butanol, wherein the method comprises fractional distillation of the crude n-butanol in a dividing wall distillation column according to claim 1.

* * * * *